Figure 1:
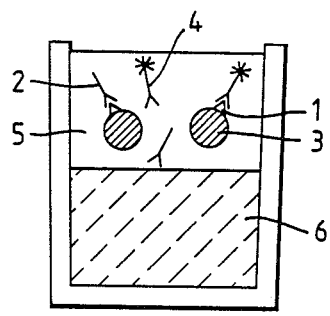

United States Patent [19]

Luotola et al.

[11] Patent Number: 4,777,145
[45] Date of Patent: Oct. 11, 1988

[54] IMMUNOLOGICAL ASSAY METHOD USING MAGNETIC PARTICLES

[75] Inventors: Juhani E. I. Luotola; Hannu Harjunmaa, both of Espoo, Finland

[73] Assignee: Labsystems Oy, Helsinki, Finland

[21] Appl. No.: 785,410

[22] Filed: Oct. 8, 1985

[30] Foreign Application Priority Data

Oct. 12, 1984 [FI] Finland .................................. 844027

[51] Int. Cl.$^4$ ........................................... G01N 33/553
[52] U.S. Cl. .................................... 436/526; 436/525; 436/546; 436/547; 436/806; 436/824
[58] Field of Search ............... 436/526, 546, 806, 525, 436/547, 824

[56] References Cited

U.S. PATENT DOCUMENTS 4,115,535  9/1978  Giaever .............................. 436/826
4,438,068  3/1984  Forrest .............................. 436/806

Primary Examiner—Robert J. Warden
Assistant Examiner—Stephen C. Wieder
Attorney, Agent, or Firm—Hopgood, Calimafde, Kalil, Blaustein & Judlowe

[57] ABSTRACT

Immunological fluorometric assay method, wherein an antigen (1) attached to magnetic particles (3) reacts in a liquid with an antibody (2) present in the sample and with an antibody (4) marked with a fluorescent substance. After the reaction, the particles are pulled by means of a magnetic field through a second (6) liquid layer onto the bottom of the measurement vessel, whereupon the particles are excited, and emitted radiation is collected through the wall of the vessel.

12 Claims, 1 Drawing Sheet

IMMUNOLOGICAL ASSAY METHOD USING MAGNETIC PARTICLES

The present invention is concerned with a fluorometric or phosphorimetric immunoassay method in which an antibody or antigen marked with a fluorescent or phoshorescent label is attached onto small polymer particles.

In solid phase fluorometric immunoassays (Solid Phase Fluoroimmunoassay) the antigen or antibody is often attached onto small pearls of polystyrene or polyacrylic. In this way, it is possible to make use of a larger face, to which the antibody or antigen adheres more readily. The antigen or antibody attached to the solid phase is allowed to react with the antibody or antigen present in the sample to be studied and with the antibody or antigen marked with a fluorescent molecule. The more there is antibody or antigen in the sample, the less of the marked antibody adheres to the solid phase. When the marked antibody or antigen remaining in the liquid phase is separated and the quantity of the marked antibody adhering to be solid phase is measured by means of a fluorometer, the concentration of the antibody or antigen in the sample is found out.

In the prior-art methods, the excess marked antibody or antigen must be washed off before the fluorometric measurement.

In certain radiometric immunoassay methods (RIA), particles containing a magnetic substance are used which are kept in their position by means of a magnetic field during the removal of liquid or washing.

The object of the present invention is to provide a fluorometric solid phase immunoassay method in which the excess label does not have to be removed out of the measurement vessel containing the pearls before the fluorometric measurement.

In the present immunological assay method the antigen (or antibody) is attached to solid particles which contain magnetic substance. These particles and antibody (or antigen respectively) labeled with fluorescent (or phosphorescent) molecule are reacted with the liquid sample containing the antibody (or antigen respectively) to be studied. In the immunological reaction the antibody of the sample and the labeled antibody react with the antigen on the magnetic particles. After the reaction the magnetic particles are pulled by means of a magnetic field against the wall or bottom of the reaction vessel through a second liquid, which is in contact but not mixed with the reaction liquid and which absorbs strongly at the excitation or emission wavelength. Then the particles are excited with appropriate radiation, and emitted fluorescent radiation is collected to the detector through the wall (or bottom) of the vessel.

In the method in accordance with the present invention, emptying of the measurement vessel and washing of the pearls can be omitted. Thus, all the transfers of liquid related to the assay are additions of liquid. This speeds up the assay and makes its automation decisively easier.

Figure 2:
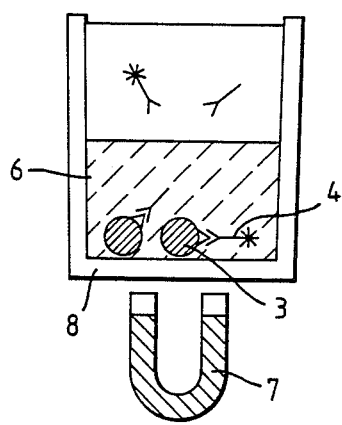
Figure 3:
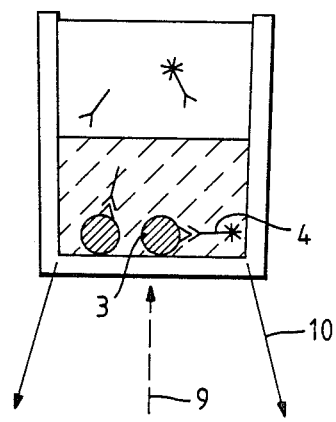

One embodiment of the method in accordance with the invention is described in more detail and referring to the attached drawing, in which FIGS. 1 to 3 illustrate different steps of the method.

Antigen 1 of the antibody 2 to be studied is attached to polymer particles 3 of a size of 0.1 to 10 m, which said particles contain a magnetic substance. The polymer is, e.g., polystyrene or polyacrylic, and the magnetic substance, e.g., iron, cobalt or nickel. The magnetic particles and fluoreschently labeled antibody 4 are mixed with the sample liquid 5.

When the polymer particles 3 are incubated with the sample 5, the corresponding antibody 2 is bound from the sample to the antigen 1 placed on the face of the polymer particles. The fluorescent conjugate 4 is, in the reaction situation, bound competitively to the face of the particles. On the other hand, the fluorescent label may be attached secondarily (by means of the sandwich technique) to the antibody (antigen) bound to the face of the particles.

At this stage (FIG. 1), the particles 3 are coated by fluorescent molecules 4 and they swim in a fluorescent conjugate, which is present as an excess quantity. In the next stage, a liquid of higher density 6 is dosed to underneath the fluorescent liquid 5, e.g. saccharose, cesium chloride, "Percoll" or "Ficoll Paque", or equivalent. The liquid of higher density is coloured appropriately so that it absorbs at the wavelengths of both fluorescence excitation and emission (at the wavelength of fluorescein-isothiocyanate, e.g., orange by means of 0.1-% methyl orange or equivalent) The second liquid layer could have been also dosed before the reaction. Optionally, the second liquid can have a density equal to the density of the reaction liquid. Also, the second liquid can be of a black color.

The fluorometer is provided with equipment 7 for generating a magnetic field (FIG. 2). By means of this equipment, the magnetic particles 3 and the fluorescent molecules 4 adhering to them are pulled onto the bottom 8 of the measurement vessel, through the coloured absorbing liquid 6 of high density. When they pass through the heavy liquid, the particles become clean of any unattached fluorescence. In the measurement situation (FIG. 3) the excitation radiation 9 is led to the magnetic-particle 3 mat formed, covered by fluorescence 4, from underneath through the bottom 8 of the vessel. The emission radiation 10 is led to the detector through the bottom as well. In addition to the heavy coloured liquid, formation of error by the fluorescent material above the said heavy liquid is also prevented by the particle mat itself, which was pulled down and which even in itself reduces the visibility of the background (shield effect).

Of course, the separation method can also be applied in other directions, besides downwards. The use of several different gradients is also quite appropriate, permitting the performance of several reactions during the transfer of the particles. In different zones there may be, for example, different antigens or antibodies, which are bound to the by-passing particles. This also permits the locating of the fluorescent conjugate in some other zone, besides the topmost one. The lowermost zone should, however, preferably be an optical barrier as well as a cleaning layer in order that a measurable signal should be produced by the attached antibody alone.

Of course, the method may also be applied to phosphorescence.

We claim:
1. An immunological assay method which comprises:
   a. attaching magnetic particles to antigens or antibodies which will react with an antibody or antigen to be studied;
   b. adding said magnetic particles to a reaction vessel containing a liquid sample suspected of containing the antibody or antigen to be studied;

c. adding to said liquid sample a fluorescently or phosphorescently labelled antibody or antigen which will react with the antigens or antibodies bound to the magnetic particles;

d. pulling the magnetic particles through a second liquid to the wall or bottom of the reaction vessel by means of a magnetic field, said second liquid being in contact with but not mixed with the liquid sample, wherein said second liquid absorbs light at the excitation or emission wavelength of the fluorescent or phosphorescent label;

e. exciting the particles with the appropriate radiation;

f. measuring the phosphorescence or fluorescence emitted by the magnetic particles; and g. correlating the phosphorescence or fluorescence measured with the prescence of labeled antigens or antibodies.

2. Method as claimed in claim 1, wherein the second liquid absorbs at the wavelength of the excitation radiation.

3. Method as claimed in claim 1, wherein the second liquid absorbs at the wavelength of the emission radiation.

4. Method as claimed in claim 1, wherein the second liquid is of black colour.

5. Method as claimed in claim 1, wherein the second liquid has a density equal to or higher than the density of the reaction solution.

6. Method as claimed in claim 5, wherein the second liquid has a density higher than the density of the reaction solution.

7. Method as claimed in claim 5, wherein the second liquid is a $CsCl_2$ solution, sucrose solution, or some other liquid solution suitable for use in density gradient centrifugings.

8. Method as claimed in claim 1, wherein the second liquid is placed into the reaction vessel before the reaction solution.

9. Method as claimed in claim 1, wherein the second liquid is placed into the reaction vessel after the reaction solution.

10. Method as claimed in claim 1, wherein, besides the reaction solution, the second liquid to be administered into the measurement vessel includes several layers of densities different from each other.

11. Method as claimed in claim 2 wherein the second liquid is of black colour.

12. Method as claimed in claim 3, wherein the second liquid is of black colour.

* * * * *